(12) United States Patent       (10) Patent No.:     US 9,126,894 B2
Rohrl                            (45) Date of Patent:    Sep. 8, 2015

(54) ELECTROCHEMICAL CELLS, AND GAS SENSOR AND FUEL CELL DEVICES COMPRISING SAME

(75) Inventor: Andreas Rohrl, Cologne (DE)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 253 days.

(21) Appl. No.: 13/103,421

(22) Filed: May 9, 2011

(65) Prior Publication Data

US 2011/0209997 A1    Sep. 1, 2011

Related U.S. Application Data

(62) Division of application No. 11/451,538, filed on Jun. 12, 2006, which is a division of application No. 10/218,262, filed on Aug. 14, 2002, now Pat. No. 7,060,169.

(51) Int. Cl.
```
H01M 8/14        (2006.01)
C07C 211/62      (2006.01)
H01M 8/18        (2006.01)
```
(Continued)

(52) U.S. Cl.
CPC .......... *C07C 211/62* (2013.01); *G01N 27/4045* (2013.01); *H01M 8/00* (2013.01); *H01M 8/0687* (2013.01); *H01M 8/1016* (2013.01); *H01M 8/188* (2013.01); *H01M 2300/0022* (2013.01); *H01M 2300/0025* (2013.01); *Y02E 60/50* (2013.01)

(58) Field of Classification Search
CPC ............ C07C 211/62; G01N 27/4045; H01M 2300/0022; H01M 2300/0025; H01M 8/00; H01M 8/0687; H01M 8/188; H01M 8/1016; Y02E 60/50
USPC ......... 429/421, 447, 464, 465, 472, 476, 477, 429/479, 482, 491, 498, 502, 530, 531
See application file for complete search history.

(56) References Cited

U.S. PATENT DOCUMENTS 4,377,446 A    3/1983  Albery
4,525,266 A    6/1985  Schmidt et al.
(Continued)

FOREIGN PATENT DOCUMENTS

DE    196 22 930 A1    12/1997
DE    102 45 337 A1    4/2004
(Continued)

OTHER PUBLICATIONS

Extended European Search Report corresponding to European Application No. 11 15 5949 dated Aug. 30, 2011.
(Continued)

*Primary Examiner* — Patrick Ryan
*Assistant Examiner* — Ben Lewis
(74) *Attorney, Agent, or Firm* — Husch Blackwell LLP

(57) ABSTRACT

An electrochemical cell for applications such as electrochemical fuel cells, or electrochemical cell gas sensors used for detection of target gas species in environments containing or susceptible to presence of same. The electrochemical cell utilizes an ionic liquid as an electrolyte medium, thereby achieving a broader range of operational temperatures and conditions, relative to electrochemical cells utilizing propylene carbonate or other conventional electrolytic media.

11 Claims, 2 Drawing Sheets

(51) Int. Cl.
*H01M 8/10* (2006.01)
*H01M 8/00* (2006.01)
*H01M 8/06* (2006.01)
*G01N 27/404* (2006.01)

(56) References Cited

U.S. PATENT DOCUMENTS

| | | | |
|---|---|---|---|
| 4,554,383 A | 11/1985 | Knifton | |
| 4,587,003 A | 5/1986 | Tantram et al. | |
| 5,164,053 A * | 11/1992 | Razaq et al. | 205/784 |
| 5,171,649 A | 12/1992 | Vaughn | |
| 5,208,112 A * | 5/1993 | Ludwig et al. | 429/419 |
| 5,338,429 A * | 8/1994 | Jolson et al. | 204/415 |
| 5,339,429 A * | 8/1994 | Tanaka et al. | 712/205 |
| 5,683,832 A * | 11/1997 | Bonhote et al. | 429/111 |
| 5,846,670 A | 12/1998 | Watanabe et al. | |
| 5,855,809 A * | 1/1999 | Angell et al. | 252/62.2 |
| 5,865,973 A | 2/1999 | Kiesele et al. | |
| 5,965,054 A | 10/1999 | McEwen et al. | |
| 7,060,169 B2 | 6/2006 | Röhrl | |
| 2001/0053472 A1 | 12/2001 | Edlund | |

FOREIGN PATENT DOCUMENTS

| | | |
|---|---|---|
| EP | 0 531 745 A2 | 3/1993 |
| WO | WO 00/15594 | 3/2000 |
| WO | WO 00/16902 | 3/2000 |

OTHER PUBLICATIONS

English translation of abstract of EP 0531745 (A2).
English translation of abstract of DE 19622930 (A1).
English translation of abstract of DE 10245337 (A1).
Carter et al., Electrochemical Reduction of Dioxygen in Room-Temperature Imidazollum Chloride-Aluminum Chloride Molten Salts, Inorg. Chem. 1991, 30, 1149-1151.
K.R. Seddon, Room-Temperature Ionic Liquids: Neoteric Solvents for Clean Catalysis, Kinetics and Catalysis, vol. 37, No. 5, 1996, pp. 693-697.
K.R. Seddon, Ionic Liquids for Clean Technology: An Update, Molten Salt Forum, vols. 5-6 (1998) pp. 53-62.
Inas M. Al Nashef et al., Electrochemical Generation of Superoxide in Room-Temperature Ionic Liquids, Electrochemical and Solid-State Letters, 4 (11) D16-D18 (2001).
Cai Qi et al., Study on sulfur dioxide electrochemical sensor using an ionic liquid, Journal of East China Normal University (Natural Science), No. 3, Sep. 2001.
Rong Wang et al., $O_2$ Gas Sensor Using Supported Hydrophobic Room-temperature Ionic Liquid Membrane-coated electrode, Chemistry Letters vol. 33, No. 1 (2004).
Rong Wang et al., A Novel Amperometric $O_2$ Gas Sensor Eased on Supported Room-Temperature Ionic Liquid Porous Polyethylene Membrane-Coated Electrodes, Electroanalysis 2004, 16, No. 1-2, pp. 66-72.
René Knake et al., Amperometric sensing in the gas-phase, Analytica Chimica Acta, Elsevier, Amsterdam, NL, vol. 549, No. 1-2 (2005), pp. 1-9.
European Patent Office's Jul. 23, 2013 Office Action corresponding to Application No. 11 155 949.8.
Advances in Electrochemistry and Electrochemical Engineering, vol. 10, John Wiley & Sons, 1976.

* cited by examiner

ELECTROCHEMICAL CELLS, AND GAS SENSOR AND FUEL CELL DEVICES COMPRISING SAME

CROSS-REFERENCE TO RELATED APPLICATIONS

This application is a divisional of U.S. patent application Ser. No. 11/451,538 filed Jun. 12, 2006; which is a divisional of U.S. patent application Ser. No. 10/218,262 filed Aug. 14, 2002 in the name of Andreas Rohrl for "Electrochemical cells, and gas sensor and fuel cell devices comprising same," which issued on Jun. 13, 2006 as U.S. Pat. No. 7,060,169, the entirety of each which is incorporated herein by reference for all purposes.

BACKGROUND

1. Field of the Invention

The present invention relates generally to electrochemical cells and to devices incorporating same, such as fuel cells, sensors, and electrochemical cell gas sensors used for detection of gases in environments containing or susceptible to presence of same, and in a specific aspect, the invention relates to an electrochemical cell utilizing ionic liquid as an electrolyte medium thereof.

2. Description of the Related Art

Gas sensors are used in many commercial and industrial applications, including workplace monitoring for the presence of toxic or otherwise hazardous or deleterious gases and in other applications where health and safety issues require detection of specific gases in the ambient environment.

In these various applications, it is frequently necessary or desirable to monitor concentration of selected gas species down to levels on the order of a few parts per million and less.

Gas sensors used in the foregoing applications include electrochemical gas sensors, which may operate to electrochemically reduce the gas species to be monitored. Alternatively, the gas sensor may operate by electrochemically oxidizing the target gas species sought to be detected. As a still further alternative, the electrochemical gas sensor may operate by indirect oxidation or reduction reaction of a compound that is produced in the gas sensor device, involving the target gas to be detected in the monitored gaseous environment.

Electrochemical gas sensors utilize sensor cells that typically contain three electrodes—the working electrode, the reference electrode and the counter electrode, although gas sensor cells are known having 2-electrode and 4-electrode structures. The electrodes are conventionally mounted within a housing that additionally contains an electrolyte, contacts and electrical wires forming electronic circuitry of the sensor, and a gas permeable membrane that keeps the electrolyte within the cell and allows the gas to contact the measuring electrode.

Electrochemical sensor cells require an electrolyte as a component of the electrochemical cell. The electrolyte performs the transport of electrical charge between the different electrodes and therefore enables an electrical current to flow. The transport of electrical charge by the electrolyte is ionic in character rather than involving charge transport by electrons.

The electrolyte usually is constituted by a liquid solvent containing electrolyte/salt component(s), wherein the solvent comprises water, or alternatively a non-aqueous solvent medium, but the electrolyte may otherwise comprise a solid electrolyte such as yttrium-stabilized zirconia (YSZ) for usage at high temperatures of about 450 to 950° C. or an ion exchange membrane such as a Nafion® membrane (commercially available from DuPont de Nemours and Company, Wilmington, Del.) that is saturated with water.

Liquid electrolytes in some instances can be 'solidified' by addition thereto of gel-forming agents, but the resultantly solidified electrolyte materials still rely on the presence of liquid solvent medium for operability, as do ion exchange systems such as the ion exchange membranes mentioned above.

Gas sensors are operationally "open systems" in the sense of requiring gas flow therethrough for detection of gas component(s) in the gas stream with which the gas sensor is contacted. One major deficiency of conventional gas sensors is the limited service life of liquid electrolytes that include gels or wetted membranes, since these materials dry out over time as solvent evaporates therefrom.

Water-based gas sensor systems are designed to be in equilibrium with ambient humidity of the environment being monitored, but their utility is generally restricted to a specific humidity range.

Solid electrolyte gas sensors are difficult to construct for efficient operation, since diffusion of gas in the solid electrolyte material is hindered in relation to liquid electrolytes, there is no transport of reactants in the solid electrolyte, and known solid electrolyte materials tend to be hygroscopic and thus are difficult to stabilize in humid environments. Additionally, solid electrolytes (i.e. solid materials providing intrinsic ion transport by usually oxide ions $O^{2-}$) need high operating temperatures. For example, yttrium-stabilized zirconia (YSZ) used in oxygen sensors does not provide sufficient ion conductivity at temperatures below 450° C.

The art therefore continues to seek improvements in electrochemical cell gas sensors.

SUMMARY OF THE INVENTION

The present invention relates generally to electrochemical cells, for applications such as electrochemical energy supplies (fuel cells, batteries, etc.) and electrochemical cell gas sensors.

In one aspect, the invention relates to an electrochemical cell including an electrolyte therein in electrical contact with electrochemical cell electrodes, wherein the electrolyte comprises an ionic liquid.

In another aspect, the invention relates to a method of increasing performance of an electrochemical cell, comprising using in such cell an electrolytic medium including an ionic liquid electrolyte.

Other aspects, features and advantages of the invention will be more fully apparent from the ensuing disclosure and appended claims.

DETAILED DESCRIPTION OF THE INVENTION, AND PREFERRED EMBODIMENTS THEREOF

Figure 1:
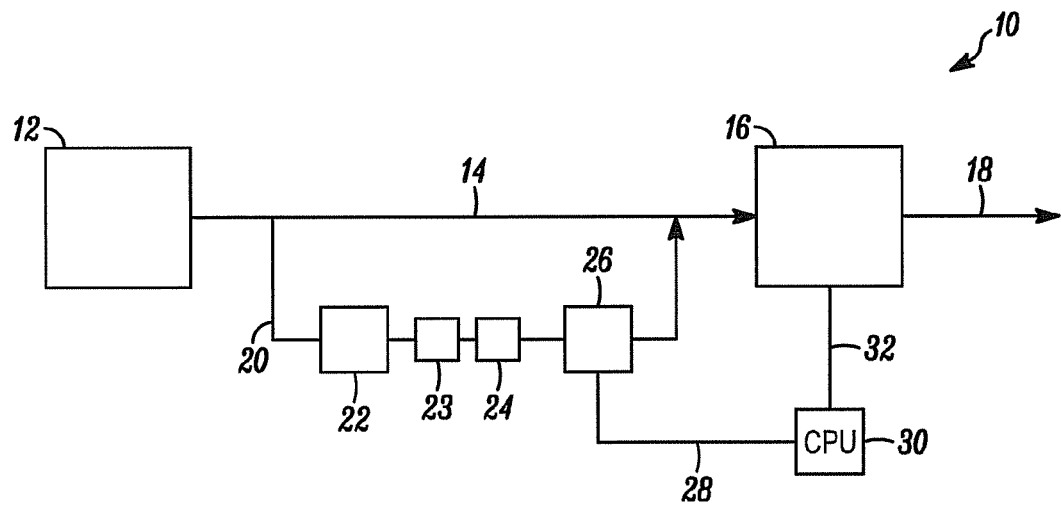
FIG. 1 is a schematic representation of a process system employing an electrochemical cell gas sensor according to the present invention, in an illustrative embodiment thereof.

The present invention relates to electrochemical cells utilizing ionic liquids as electrolyte media.

As used herein, the term "ionic liquid" means a salt comprising at least one cation and one anion and being liquid at temperatures below 250° C., preferably below 100° C., and most preferably below 50° C. (e.g., 20-30° C.).

The ionic liquids employed in the broad practice of the invention may be of any suitable type, and include those disclosed in: International Publication No. WO 00/16902 for "IONIC LIQUIDS;" International Publication No. WO 00/15594 for "PROCESS FOR MAKING AROMATIC ALDEHYDES USING IONIC LIQUIDS;" U.S. Pat. No. 4,554,383; Seddon, K. R., Molten Salt Forum, 5-6, pp. 53-62 (1998); and Seddon, K. R., Kinetics and Catalysts, 37, 5, pp. 743-748 (1996), the disclosures of which hereby are incorporated herein by reference in their respective entireties.

The electrochemical cell devices of the present invention include electrochemical cell gas sensors and fuel cells, wherein ionic liquid is employed as an electrolyte medium, having utility in many environments including but not limited to:
 a) environments having broad humidity range, preferably environments having low relative humidity;
 b) environments having high air flow; and
 c) environments operating at higher temperatures.

Additionally, the electrochemical cell devices of the present invention include electrochemical cell gas sensors, having potentially smaller physical dimensions as compared to current electrochemical cell gas sensing devices using aqueous and organic solvent electrolyte. Such smaller dimensions are possible, because unlike current electrochemical sensors, solvent evaporation issues are substantially non-existent allowing for reduced amounts of electrolyte and elimination of reservoir(s) for solvent replacement.

By minimizing the evaporation issue, the electrochemical cell gas sensors of the instant invention are advantageously available for detecting a broader range of target compounds and sensor lifetime is no longer restricted by the amount of electrolyte.

In one aspect, the electrochemical cell of the invention comprises an electrochemical cell gas sensor, in which an ionic liquid is employed as an electrolyte. The electrochemical cell gas sensor may be of any suitable fabrication or construction, e.g., comprising a housing, with two or more electrodes operatively arranged in an interior volume of the housing and communicating with electrical circuitry means (e.g., contacts, wires, conductive films, circuit components, etc.) and the ionic liquid electrolyte.

The ionic liquid may be of any suitable type and may have a melting point that is ≤250° C. The melting point of the ionic liquid may be above or below the operating temperature of a particular process.

The vapour pressure of the ionic liquids of the instant invention at room temperature is negligible to non-measurable, as compared to electrolyte materials of the prior art (such as water, acrylonitrile, propylene carbonate, and the like).

Illustrative ionic liquids useful as electrolyte materials in electrochemical cell gas sensors in the practice of the present invention include, without limitation, salts with imidazolium or pyridinium cations. The cations that may be usefully employed in a given application of the invention include cations with alkyl and/or aryl substituents, optionally wherein the alkyl and/or aryl substituents are themselves further substituted, e.g., with halo, loweralkyl ($C_1$-$C_4$), hydroxyl, amine, etc.), such cations being capable of forming salts when reacted with corresponding anions.

Illustrative anions for such purpose include, without limitation, halides (chlorides, iodides, bromides, fluorides), nitrates, nitrites, tetrafluoroborates, hexafluorophosphates, trifluoromethanesulfonates and other polyfluoroalkanesulfonates, e.g., nonaflate, bis(trifluoromethylsulfonyl)imides, methylsulfates, acetates, fluoroacetates and other anions of fluoroalkanoic acid.

In one embodiment, the ionic liquid electrolyte comprises at least one salt selected from the group consisting of salts with the general formula $C^+A^-$ where $C^+$ represents a quaternary ammonium and/or phosphonium salt and $A^-$ represents any known anion that can form ionic liquids in the meaning described in the present invention. Non-limiting examples include methyl-octyl-imidazolium-chloride and butyl-methyl-imidazolium-bis-trifluoromethane-sulfonimide.

The low vapour pressure ionic liquids in gas sensor electrochemical cells of the present invention may include compounds as described above, in single salt electrolyte compositions, as well as use of same and similar compounds in mixtures together with varying amounts of aluminum halides, preferably aluminum chloride, or other salts that increase the conductivity of the electrolytic medium, or otherwise enhance the gas detection sensitivity of the gas sensor electrochemical cell.

The electrochemical cell gas sensor of the invention may be constructed and arranged in any appropriate manner to carry out the sensing of the target gas species in a gaseous environment containing or susceptible to the presence of same. The fabrication and manufacture of electrochemical cell gas sensors is more fully described in Advances in Electrochemistry and Electrochemical Engineering, Volume 10, John Wiley & Sons, 1976, and the electrochemical cell gas sensor assembly in accordance with the invention may include a chemically selective filter for the electrochemical gas sensing cell, to remove interferent gas components that would otherwise interfere with or preclude measurement of the target gas species in the gas environment being monitored by the gas sensor assembly.

For example, the electrochemical cell gas sensor may be constructed and arranged to electrochemically reduce the gas species to be monitored, so that the monitoring operation involves chemical reduction of the target gas species. Alternatively, the electrochemical cell gas sensor may operate by electrochemically oxidizing the target gas species sought to be detected. As a still further alternative, the electrochemical cell gas sensor may operate by indirect oxidation or reduction reaction of a compound that is produced in the gas sensor device, involving the target gas to be detected in the gas environment being monitored for the presence of the target gas species.

The electrochemical cell gas sensor may be configured to utilize a gas sensor cell containing three electrodes—the working electrode, the reference electrode and the counter electrode, although gas sensor cells having 2-electrode and 4-electrode structures may alternatively be employed. The electrodes are mounted within a housing containing the ionic liquid electrolyte, with the electrodes being coupled in circuit-forming relationship with contacts and electrical wires forming the electronic circuitry of the sensor.

The superiority of the ionic liquid electrolyte medium in the electrochemical cell gas sensor of the present invention has been demonstrated by relative weight loss tests in which propylene carbonate, a widely used electrolyte of prior art electrochemical cell gas sensors, and ionic liquids of the present invention (e.g. methyl-octyl-imidazolium-chloride and butyl-methyl-imidazolium-bis-trifluoromethane-sulfonimide) were evaluated at 80° C. After only 5 days at such temperature of 80° C., propylene carbonate, having a boiling point of 240° C., was totally evaporated, while the ionic liquids of the present invention were of unchanged mass within the accuracy of the measurement apparatus. These results evidence an unexpected advantage and superiority of the ionic liquids of the present invention over electrolyte characteristic of prior art electrochemical cell gas sensors.

In general, useful electrolytes for electrochemical cells must have an electrical conductivity of at least $10^{-5}$ ohm$^{-1}$ cm$^{-1}$. The electrical conductivity of the ionic salts of the present invention are typically on the order of 0.01 ohm$^{-1}$ cm$^{-1}$, three orders of magnitude above such electrolytic threshold, providing unexpectedly superior performance of electrochemical cell gas sensors utilizing same. In general, ionic liquids which are preferred for use as electrolyte in the practice of the present invention have an electrical conductivity of at least $10^{-3}$ ohm$^{-1}$ cm$^{-1}$ and such ionic liquids most preferably include those having an electrical conductivity of at least $10^{-2}$ ohm$^{-1}$ cm$^{-1}$.

The invention therefore provides an electrochemical cell gas sensor including a gas sensor cell in which an 'ionic liquid' is employed as an electrolyte, e.g., a salt having a melting point below 100° C. and preferably a liquid at room temperature. In contrast to prior art liquids used as electrolyte media, the ionic liquid systems of the invention are characterized by negligible vapour pressure of the electrolyte, and an extremely high electrolytic character since the ionic liquids are constituted by ions.

In another aspect, the invention provides electrochemical fuel cells using ionic liquids as solvent/electrolyte media.

Fuel cells are electrochemical cells consisting of two electrodes connected with an ion-conducting electrolyte. The electrodes usually have a porous structure and are designed to allow very close contact between a gas (the fuel), the electrolyte and the catalyst powder that catalyses the chemical reactions. Oxidation and reduction are separated so that they occur at different electrodes, and the electric circuit is closed by ion transport from one electrode through the electrolyte to the other electrode.

The fuel cells of the present invention in one aspect thereof may be fabricated with cathode and anode elements in an assembly in which the ionic liquid electrolyte medium is disposed between the respective electrodes, in an electrolyte/electrode assembly, with the respective cathode and anode elements have backing layers on their outer surfaces providing pathways for gas access to the respective electrode. On the outer surfaces of the respective backing layers are provided current collector plates including a cathode current collector plate on the cathode-backing layer, and an anode current collector plate on the anode-backing layer. The current collectors are in turn coupled with circuitry including load or output device(s) that utilize the electrical output of the fuel cell.

In contrast to conventional fuel cells that utilize electrolytes that highly restrict the operating range of temperature of the fuel cell (e.g., phosphoric acid fuel cells (PAFCs), using phosphoric acid as electrolyte and operated at about 200° C.; molten carbonate fuel cells (MCFC), using molten carbonates as electrolyte and operated at 500 to 600° C.; solid polymer membrane fuel cells (SPMFC), using conducting polymers as electrolyte and operated below 80° C.; alkaline fuel cells (AFC), using concentrated alkalai brine and operated below 100° C.; and solid oxide fuel cells (SOFC) operated at temperatures close to 1000° C.), fuel cells utilizing ionic liquid electrolytes in accordance with the present invention can operate at substantially lower temperatures and over significantly wider temperature ranges in which the performance of the prior art fuel cells would be deficient or even non-existent.

The ionic liquids used as electrolyte media in fuel cells of the present invention may be of any suitable type, including the ionic liquid electrolytes described hereinabove in the preceding discussion of electrochemical cell gas sensors utilizing ionic liquid electrolytes in accordance with the present invention.

The features and advantages of the present invention are more fully appreciated with respect to the following embodiments, described in reference to the drawings.

FIG. 1 is a schematic representation of a process system 10 employing an electrochemical gas sensor according to the present invention, in an illustrative embodiment thereof.

The FIG. 1 process system 10 includes a supply 12 of a source gas. The supply 12 may include a process unit that generates the target gas (i.e., the gas component to be monitored by the electrochemical cell gas sensor) in mixture with other gas components, as a multicomponent gas mixture. Alternatively, the supply 12 of the source gas may be a gas environment that is subject to ingress or contamination by the target gas, e.g., as a toxic, or otherwise hazardous or undesirable gas species in the particular environment. The source gas, containing the target gas as a component thereof, flows from supply 12 in line 14 to the abatement processing unit 16 in which the source gas is treated to remove the target gas therefrom.

A target gas-depleted stream is discharged from the abatement-processing unit 16 in line 18, and may be passed to a further downstream process or final disposition, as required.

A side stream of the source gas from line 14 is flowed in line 20, under the action of motive fluid driver 22, through dust filter 23, interferent species filter 24 and gas sensor 26, being returned to line 14 downstream of gas sensor 26, as shown. The dust filter 23 removes particulates from the source gas, and the interferent species filter 24 removes gas components from the dust-depleted source gas that may interfere with the accurate sensing of the target gas by the electrochemical cell gas sensor. By this arrangement, an interferent-free gas composition, including the target gas species, is flowed from the interferent species filter 24 to the electrochemical cell gas sensor 26.

The electrochemical cell gas sensor 26 monitors the concentration of the target gas species in the side stream and generates a corresponding response signal correlative to the sensed concentration of the target gas species. The response signal is transmitted in signal transmission line 28 to central processing unit (CPU) 30, which in turn generates a corresponding control signal that is transmitted in control signal line 32 to the abatement-processing unit 16. The control signal in line 32 may be employed to modulate the gas processing operation in abatement processing unit 16 to abate the target gas species.

As an illustrative example, if phosgene were the target gas species in the source gas, and such target gas species is abated by chemical reaction thereof with a chemical reagent in the abatement processing unit 16, the amount of the chemical reagent may be modulated in response to the sensed concentration of the phosgene in the source gas, to effect substantially complete removal of the phosgene from the gas stream treated in abatement processing unit 16. In other abatement operations, the process conditions (e.g., temperatures, pressures, flow rates, retention time, etc.) in the abatement processing unit 16 may be modulated to effect the desired reduction in the concentration of the target gas species in the effluent stream being treated.

Figure 2:
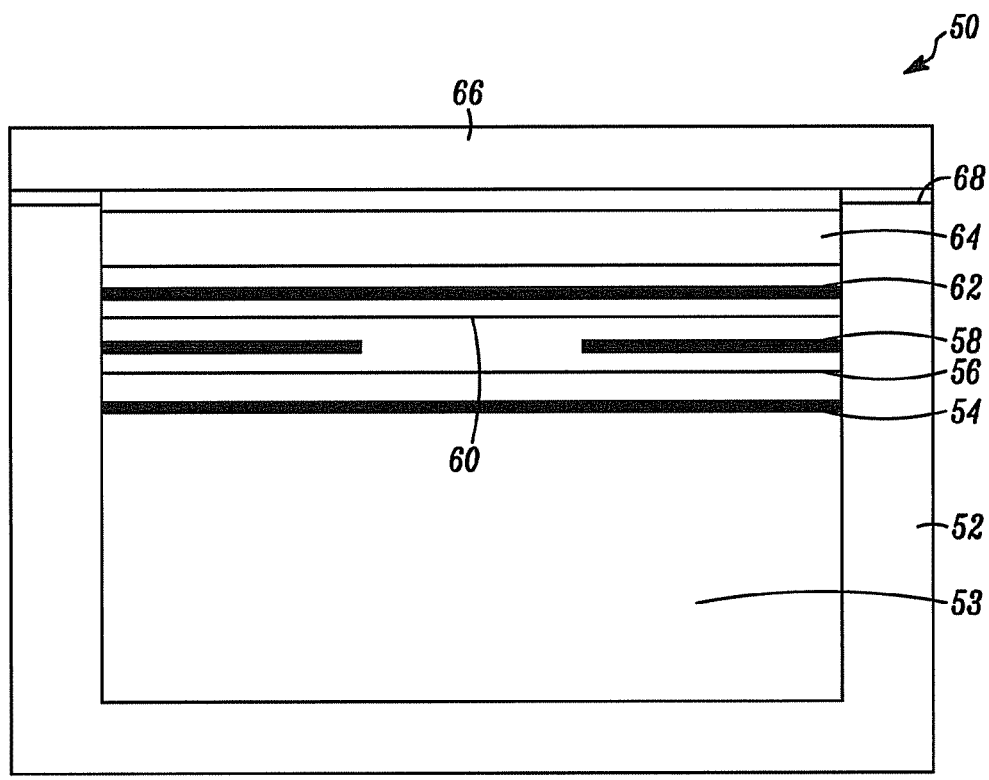
FIG. 2 is a schematic representation of an electrochemical cell gas sensor and filter unit according to one embodiment of the invention.

FIG. 2 is a schematic representation of an electrochemical cell gas sensor 50 according to one embodiment of the invention.

The electrochemical cell gas sensor 50 comprises a housing 52 formed of a suitable material of construction, e.g., metal, ceramic, polymer, etc. defining therewithin an interior volume. The interior volume of the housing includes an electrolyte compartment 53 containing an ionic liquid electrolyte in accordance with the invention, and an electrode assembly including a counter electrode 54, a reference electrode 58 and a working electrode 62. The counter and reference electrodes are separated by separator member 56, and the reference and working electrodes are separated by separator member 60.

Overlying the electrode assembly is an interferent species filter 64 for removing interferent species from the source gas flowed therethrough. A dust filter 66 is joined to the housing 52 at the upper end of the housing walls, as shown, being sealed to the top edges of the walls by bond 68. The bond 68 is formed of a suitable adhesive or sealant medium, and joins the dust filter 66 to the housing 52 in a leak-tight manner, so that source gas flowed through the filter enters the interferent species filter 64 and is prevented from bypassing the filtration and sensing elements in the housing interior volume.

It will be recognized that the electrochemical cell gas sensor 50 is schematically illustrated for ease of description, and does not show the electrical leads to the electrode elements in the housing or other ancillary structure, but based on such description, the electrochemical cell gas sensor 50 may be readily constructed by those skilled in the art, to effect gas sensing operation that is accurate and reproducible for monitoring of the target gas species in the source gas.

Figure 3:
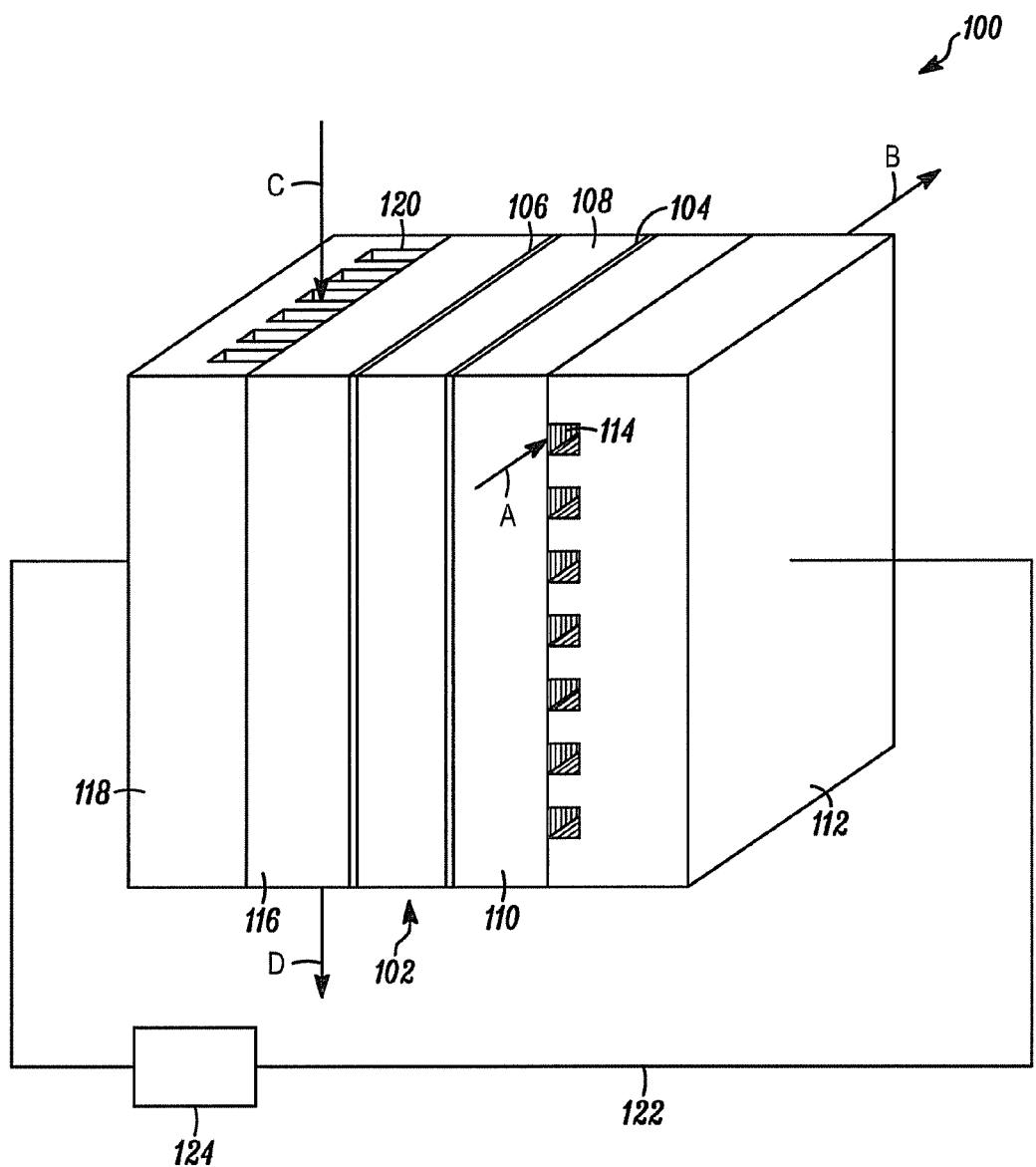
FIG. 3 is a simplified schematic representation of an electrochemical fuel cell according to another embodiment of the invention.

FIG. 3 is a simplified schematic representation of an electrochemical fuel cell 100 according to another embodiment of the invention.

The electrochemical fuel cell 100 as illustrated includes an ionic liquid electrolyte compartment 108 containing an ionic liquid electrolyte 102 in accordance with the present invention, and arranged so that the ionic liquid electrolyte in the electrolyte compartment 108 is in contact with anode 106 and cathode 104.

On the outer surface of the anode (the main surface opposite the surface in contact with the electrolyte) is disposed an anode backing layer 116. In like manner, the outer surface of the cathode 104 has disposed in contact therewith a cathode-backing layer 110.

Outwardly of the backing layers 116 and 110 is provided an anode current collector 118 in contact with the anode backing layer 116, and a cathode current collector 112 in contact with the cathode backing layer 110, as shown.

The backing layers 116 and 110 are formed of suitable material having pathways therein for gas access to the corresponding electrode with which the backing layer is in contact.

The anode current collector 118 is formed with fuel flow passages 120 therein, accommodating flow of fuel into the passages 120 in the direction indicated by arrow C, with the spent/unused fuel being discharged from such passages in the direction indicated by arrow D. The fuel may comprise hydrogen or any other fuel medium.

The cathode current collector 112 is correspondingly formed with oxidant flow passages 114 therein, into which oxidant is flowed in the direction indicated by arrow A in FIG. 3, and from which spent/unused oxidant is discharged in the direction indicated by arrow B. The oxidant may be of any suitable type, e.g., oxygen, air, oxygen-enriched air, ozone, etc.

The anode and cathode current collectors 118 and 112 in the FIG. 3 fuel cell are coupled with electrical circuitry, schematically represented in FIG. 3 by circuit wire 122, interconnecting the fuel cell with a load or output device 124 of desired type.

The fuel cell structure shown in FIG. 3 is highly simplified in character for purposes of illustration, and it will be appreciated that fuel cell apparatus in accordance with the present invention may be fabricated and arranged in a wide variety of conformations and embodiments. The fuel cell apparatus may include a fuel cell stack utilizing a plurality of fuel cell unit structures as shown in FIG. 3, joined together with bipolar current collector plates and end plates, as is known in the art for achieving economies of scale in use of fuel cell elements.

The features, aspects and advantages of the present invention are further shown with reference to the following non-limiting examples relating to the invention.

EXAMPLES

Example 1

An electrochemical cell gas sensor, comprising a gas sensor such as schematically described above, allows for the measurement of hydrogen sulfide ($H_2S$) concentrations in a gas mixture. The sensor comprises a measuring electrode made of silver (Ag), a reference electrode made of silver (Ag), and a counter electrode made of silver (Ag). Further, the sensor comprises an electrolyte consisting of an ionic liquid, namely ethyl-methyl-imidazolium-trifluorormethane-sulfonate. Concentrations of 20-ppm hydrogen sulfide give rise to a signal current of 0.01 mA. The response time is typically less than 30 s after initial exposure to the gas.

Example 2

An electrochemical cell gas sensor, comprising a gas sensor such as schematically described above, allows for the measurement chlorine ($Cl_2$) concentrations in a gas mixture. The sensor comprises a measuring electrode made of gold (Au), a reference electrode made of platinum (Pt), and a counter electrode made of platinum (Pt). Further, the sensor comprises an electrolyte consisting of an ionic liquid, namely butyl-methyl-imidazolium-bis-trifluoromethane-sulfonimide. Concentrations of 1-ppm chlorine give rise to a signal current of 0.2 µA. The response time is typically 30 s after initial exposure to the gas.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. An electrochemical gas sensor assembly comprising:
a housing;
a first and a second electrode positioned within the housing;
a substantially solvent-free, ionic liquid electrolyte contained within the housing in electrical contact with the electrodes; and
a gas access port,
wherein the substantially solvent-free, ionic liquid electrolyte comprises methyl-octyl-imidazolium-chloride, or butyl-methyl-imidazolium-bis-trifluoromethane-sulfonimide, or mixtures thereof,
wherein the substantially solvent-free, ionic liquid electrolyte is substantially free of additives wherein the substantially solvent-free, ionic liquid electrolyte is weight-stable after remaining 5 days at a temperature of 80° C.

2. The electrochemical gas sensor assembly according to claim 1, wherein the substantially solvent-free, ionic liquid electrolyte comprises at least one salt having a melting point less than about 100° C.

3. The electrochemical gas sensor assembly according to claim 1, wherein the substantially solvent-free, ionic liquid electrolyte comprises one salt.

4. The electrochemical gas sensor assembly according to claim 1, wherein the substantially solvent-free, ionic liquid electrolyte comprises a mixture of salts.

5. The electrochemical gas sensor according to claim 1, wherein the substantially solvent-free, ionic liquid electrolyte has a negligible vapor pressure.

6. The electrochemical gas sensor according to claim 1, wherein the ionic liquid electrolyte has an electrical conductivity of at least $10^{-3}$ $ohm^{-1}$ $cm^{-1}$.

7. The electrochemical gas sensor assembly according to claim 1, wherein the ionic liquid electrolyte has an electrical conductivity of at least $10^{-2}$ $ohm^{-1}$ $cm^{-1}$.

8. The electrochemical gas sensor assembly according to claim 1, wherein the ionic liquid electrolyte further comprises an aluminum halide.

9. The electrochemical gas sensor assembly according to claim 1 further comprising a three-electrode arrangement including a working electrode, a reference electrode and a counter electrode.

10. The electrochemical gas sensor assembly according to claim 1 further comprising a four-electrode arrangement.

11. An electrochemical gas sensor assembly having a housing comprising: a substantially solvent-free, ionic liquid electrolyte, and
at least a first and a second electrode in contact with the ionic liquid electrolyte,
wherein the substantially solvent-free, ionic liquid electrolyte comprises methyl-octyl-imidazolium-chloride, or butyl-methyl-imidazolium-bis-trifluoromethane-sulfonimide, or mixtures thereof,
wherein the substantially solvent-free, ionic liquid electrolyte is substantially free of additives
wherein the first electrode has a backing layer thereon providing passageways therein for gas access there,
wherein the second electrode has a backing layer thereon providing passageways therein for gas access thereto,
wherein the ionic liquid electrolyte is weight-stable after 5 days at a temperature of 80° C.

* * * * *